United States Patent [19]

Bell

[11] Plant 4,378

[45] Feb. 13, 1979

[54] ALMOND TREE

[75] Inventor: James C. Bell, 1699 East Ave., Chico, Calif. 95926

[73] Assignees: James C. Bell; Elberta F. Bell, both of Chico, Calif.

[21] Appl. No.: 841,318

[22] Filed: Oct. 11, 1977

[51] Int. Cl.[2] ..... A01H 5/03

[52] U.S. Cl. ..... Plt./30

[58] Field of Search ..... Plt./30

*Primary Examiner*—Robert E. Bagwill

*Attorney, Agent, or Firm*—Roger B. Webster

[57] ABSTRACT

An almond tree which is dense, medium size, vigorous, spreading in branching habit, abundantly foliated with medium size, medium green, acuminate leaves having a crenate margin, blooms early with pink flowers, and is a regular and heavy producer—in clusters on short spurs—of large, elongated, paper shell, well-sealed nuts which hang well on tree and have a medium harvest period and a relatively high percentage of kernel to nut.

1 Drawing Figure

BACKGROUND OF THE VARIETY

1. Field of the Discovery

The present new and distinct variety of almond tree is embraced by Class 30, Plants, of the U.S. Patent Office MANUAL OF CLASSIFICATION.

2. Prior Varieties

Among the existent varieties of almond trees which are known to me are those mentioned herein for the purpose of comparison; to-wit, Ne Plus Ultra and Nonpareil (both unpatented).

ORIGIN OF THE VARIETY

While the origin of the present variety of almond tree is unknown, it was discovered by me—when inspecting an almond orchard (which I previously owned) located near Durham, Butte County, Calif.—growing as an individually distinct tree in a row of Ne Plus Ultra almond trees; my attention having been particularly attracted to such individually distinct tree by reason of its different appearance in tree form, dense foliage, and a total absence of brown rot. Also, adjacent trees of the Ne Plus Ultra bore a heavier crop—indicative of the fact that such individually distinct tree was a pollenizer. Upon discovery of such individually distinct tree, I took buds therefrom preparatory to asexual reproduction of the variety.

ASEXUAL REPRODUCTION OF THE VARIETY

The present variety of almond tree was asexually reproduced by me by budding on other trees in the almond orchard located as aforesaid; such bud-produced asexual reproductions having—in maturity—run true to the original tree in all respects.

SUMMARY OF THE VARIETY

The present variety of almond tree is dense, medium size, vigorous, spreading in branching habit, abundantly foliated with medium size, medium green, acuminate leaves having a crenate margin, blooms early with pink flowers, and is a regular and heavy producer—in clusters on short spurs—of large, elongated, paper shell, well-sealed nuts which hang well on tree and have a medium harvest period and a relatively high percentage of kernel to nut.

The present variety of almond tree is further characterized—particularly in comparison to the Ne Plus Ultra—by a branching habit which, while essentially spreading, is more upright and hence easier to knock at harvest, by thicker foliage, by pink bloom rather than white bloom, by an apparent immunity to brown rot, and by nuts easier to hull and having a softer shell; the present variety being in bloom four or five days before the Nonpareil, and in harvest with said Ne Plus Ultra.

The present variety of almond tree is further characterized by its excellence as a pollenizer, especially for the Nonpareil which blooms shortly after the onset of the bloom of said present variety.

BRIEF DESCRIPTION OF THE DRAWING

The drawing is an illustration, by photographic reproduction in color, of twigs with leaves, nuts on one twig, and—separately—nuts in hull, nuts out of hull, and kernels out of shell.

DESCRIPTION OF THE VARIETY

The botanical details of this new and distinct variety of almond tree—with color definitions (except those in common color terms) referenced to Maerz and Paul Dictionary of Color—are as follows:

Tree:
- *Density.*—Dense.
- *Size.*—Medium.
- *Vigor.*—Vigorous.
- *Wood.*—Soft.

Trunk:
- *Form.*—Medium.
- *Texture.*—Shaggy.

Branches:
- *Form.*—Medium.
- *Texture.*—Medium.
- *Lenticels Number.*—Medium.
- *Size.*—Medium.
- *Branching Habit.*—Spreading (but more upright than Ne Plus Ultra).
- *Color.*—New Wood — Red. Mature Wood — Brown.

Foliage:
- *Quantity.*—Abundant.

Leaves:
- *Size.*—Medium. Average length — 2½". Average width — ¾".
- *Shape.*—Acuminate.

*Thickness.*—Medium.
*Texture.*—Smooth.
*Margin.*—Crenate.
*Petiole.*—Medium length — average ¾". Medium thickness.
*Glands.*—Number — 1 to 3. Alternate. Usually positioned on petiole, sometimes 1 to 2 on base of blade.
*Color.*—Top Side — Medium green (23-J-9). Under Side — Lighter green (22-J-7).

Bloom:
*Amount Of Bloom.*—Average.
*Color.*—Pink.
*Blooming Period.*—Early — 5 days before Nonpareil.

Crop:
*Bearing.*—Regular bearer.
*Productivity.*—Heavy.
*Distribution Of Nuts On Tree.*—In clusters on short spurs.
*Harvest Period.*—Medium — same as Ne Plus Ultra.
*Tenacity.*—Hangs well on tree. Easy to harvest. Easy to hull.

Hull:
*Outer Surface.*—Smooth.
*Form.*—Regular.
*Thickness.*—Medium.
*Flesh.*—Fleshy.
*Suture.*—Flat depressed.
*Color.*—Parrot green (21-L-6) with fine silvery pubescence.
*Dehiscence.*—Opens freely.
*Splitting.*—Along suture.

Nut:
*Size.*—Large. Average length — 1½". Average width (including wing) — 13/16". Average thickness — 9/16". Average weight — approximately 35 to an ounce.
*Form.*—Length/Width — Elongated. Width/-Thickness — Medium.
*Shell.*—Paper. Soft. Thin. Smooth. Outer Shell — Largely missing. Inner Shell — Soft. Well sealed.
*Color.*—Macaroon brown (12-H-7).
*Stem Scar.*—Small.
*Wing.*—Broad. Thin. Tapered toward base.

*Inner Surface.*—Light.
*Percentage Of Kernal To Nut.*—68.6% (1976).

Kernel:
*Size.*—Large. Average length — 1⅛". Average width — ½". Average thickness — 7/16".
*Form.*—Length/Width — Elongated. Width/-Thickness — Medium.
*Base.*—Ventrally oblique.
*Stem Scar.*—Small.
*Texture.*—Smooth when fresh. Somewhat wrinkled when dry.
*Pellicle.*—Thin.
*Pubescence.*—Smooth.
*Color.*—Centennial brown (13-K-8).
*Number Of Doubles.*—Few.
*Defective Kernels.*—None observed.
*Flavor.*—Normal.
*Quality.*—Good.

Resistance to Disease: Apparent resistance to brown rot.

The almond tree and its nuts herein described may vary in slight detail due to climatic and soil conditions under which the variety may be grown; the present description being of the variety as grown in the Sacramento Valley of California.

I claim:

1. A new and distinct variety of almond tree, substantially as illustrated and described, which is dense, medium size, vigorous, spreading in branching habit, abundantly foliated with medium size, medium green, acuminate leaves having a crenate margin, blooms early with pink flowers, and is a regular and heavy producer—in clusters on short spurs—of large, elongated, paper shell, well-sealed nuts which hang well on tree, and have a medium harvest period and a relatively high percentage of kernel to nut; the present variety, in particular comparison to the Ne Plus Ultra, being characterized by a branching habit which, while essentially spreading, is more upright and easier to knock at harvest, by thicker foliage, by pink bloom rather than white bloom, by an apparent immunity to brown rot, and by nuts easier to hull and having a softer shell; the present variety being in bloom four or five days before the Nonpareil and in harvest with the Ne Plus Ultra.

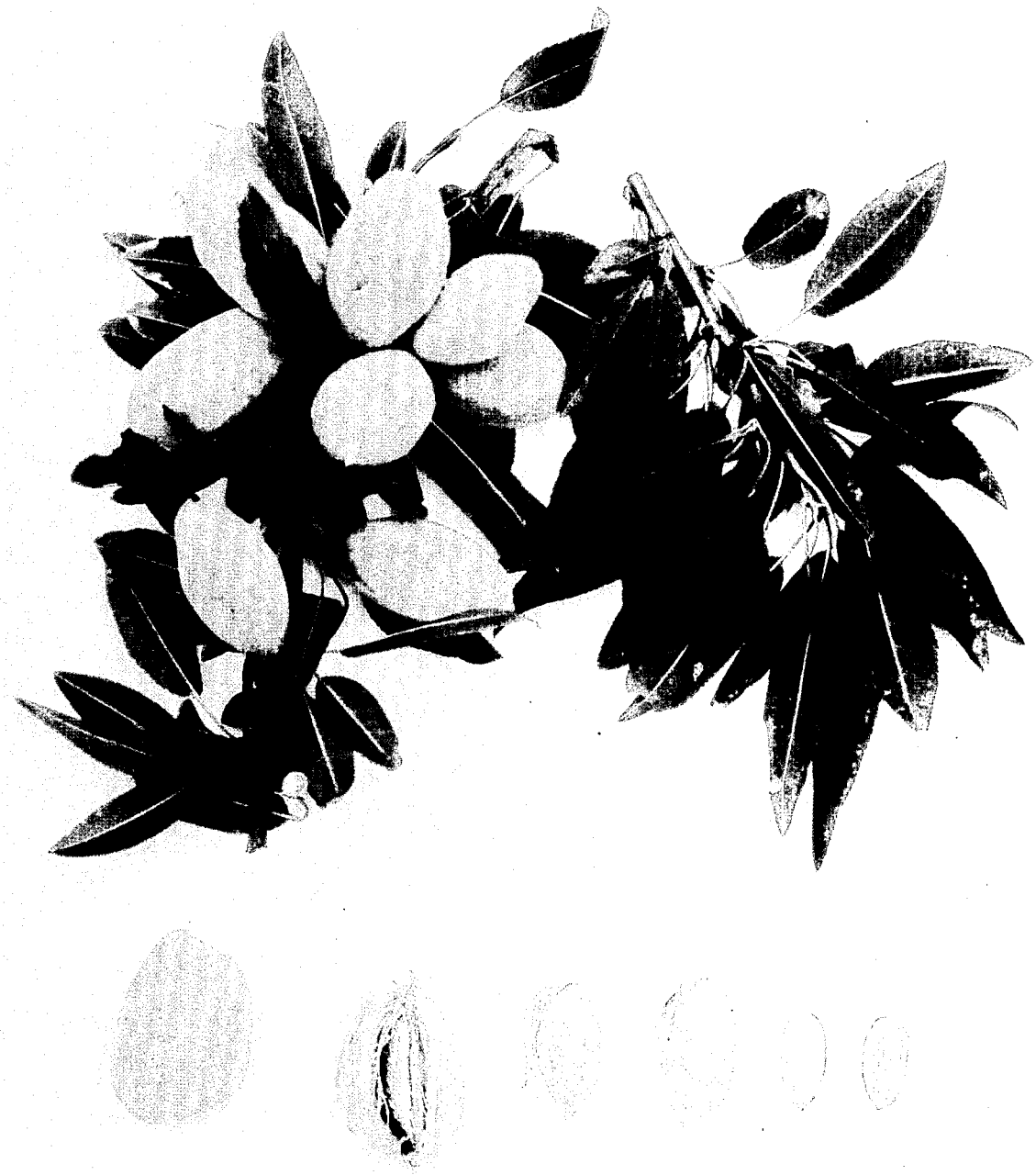

* * * * *